United States Patent [19]

Wuest et al.

[11] Patent Number: 5,041,691

[45] Date of Patent: Aug. 20, 1991

[54] ALDOL CONDENSATION OF NITROPARAFFINS

[75] Inventors: Willi Wuest, Ratingen; Rainer Eskuchen, Duesseldorf; Herbert Esser, Troisdorf, all of Fed. Rep. of Germany

[73] Assignee: Henkel Kommanditgesellschaft auf Aktien, Duesseldorf

[21] Appl. No.: 345,517

[22] Filed: May 1, 1989

[30] Foreign Application Priority Data

Apr. 30, 1988 [DE] Fed. Rep. of Germany ....... 3814772

[51] Int. Cl.$^5$ .......................................... C07C 205/15
[52] U.S. Cl. ..................................... 568/704
[58] Field of Search ........................................ 568/704

[56] References Cited

U.S. PATENT DOCUMENTS

| 3,723,546 | 3/1973 | Bachman et al. | 568/704 |
| 4,241,226 | 12/1980 | Adrian | 568/704 |
| 4,496,772 | 1/1985 | Lai | 568/704 |

FOREIGN PATENT DOCUMENTS 648889  9/1962  Canada ............................... 568/704

OTHER PUBLICATIONS

Vanderbilt et al., "Industrial and Engineering Chemistry", vol. 32, Jan. 1940, pp. 34–38.
Chemical Abstract 81,119937y, (1974).

*Primary Examiner*—Werren B. Lone
*Attorney, Agent, or Firm*—Ernest G. Szoke; Wayne C. Jaeschke; Henry E. Millson, Jr.

[57]  ABSTRACT

A process for reacting nitroparaffins with formaldehyde in the presence of potassium hydroxide by aldol condensation which can be carried out continuously or discontinuously and on a large scale. This is achieved by mixing the nitroparaffin, aqueous aldehyde solution and potassium hydroxide in the absence of organic solvents and carrying out the reaction while maintaining the temperature between −5° and +20° C.

18 Claims, No Drawings

ALDOL CONDENSATION OF NITROPARAFFINS

BACKGROUND OF THE INVENTION

1. Field of the Invention

This invention relates to a process which can be carried out on a large-scale for the aldol condensation of nitroparaffins with aldehydes, particularly formaldehyde.

2. Statement of Related Art

The base-catalyzed reaction of nitroparaffins with aldehydes, particularly formaldehyde, is known. For example, in the case of nitromethane all the acid hydrogen atoms are substituted by formaldehyde as hydroxymethyl groups in the presence of bases. The reaction is highly exothermic and furthermore side-reactions can occur if certain temperature limits are exceeded, because both the aldehydes and the nitroparaffins react with themselves in the presence of bases at high temperatures. It is therefore usual for the process to be carried out in an organic solvent or in a high dilution.

The reaction of aqueous formaldehyde solution with aqueous sodium hydroxide at temperatures of 5° to 10° C. in gram-amounts is described in the Japanese Patent Application 74/70,911, cited in "Chemical Abstracts" 81, 119937y, (1974).

DESCRIPTION OF THE INVENTION

Other than in the operating examples, or where otherwise indicated, all numbers expressing quantities of ingredients or reaction conditions used herein are to be understood as modified in all instances by the term "about".

In view of the above prior art, there is a pressing need for a commercially viable large-scale process which can be carried out as either a batch or continuous process for the reaction of nitroparaffins with aldehydes. One object of the present invention is to develop such a process for the reaction of nitroparaffins with aldehydes in the presence of potassium hydroxide in a commercially practical large-scale continuous or discontinuous process.

When the process disclosed in the above Japanese Patent Application 74/70,911 was scaled up to the pilot plant stage, deposits formed in some sections of the reaction equipment necessitating cleaning of the equipment after every reaction batch.

When the above process was carried out using potassium hydroxide instead of sodium hydroxide, no deposits formed anywhere in the equipment. Accordingly, it was surprisingly discovered that a commercially practical process resulted from the use of potassium hydroxide, while the use of the prior art sodium hydroxide resulted in a process that was not commercially feasible.

Accordingly, the present invention relates to a process for the reaction of nitroparaffins with aldehydes in the presence of potassium hydroxide by aldol condensation in which a nitroparaffin, aqueous aldehyde solution, and potassium hydroxide are mixed in the absence of organic solvents, and the reaction is carried out on a large scale either continuously or discontinuously at a temperature in the range of from −5° to +20° C.

For the carrying out of the present process, the individual reaction components are first introduced into a reaction vessel, preferably in the shape of a tube equipped with means for external cooling such as a heat exchanger. In a preferred embodiment the aqueous aldehyde is first mixed with the alkali metal hydroxide, care being taken that the temperature of the mixture does not exceed 10° C. because disproportionation (Cannizarro reaction) can otherwise occur. The nitroparaffin is then added to this mixture and the resulting reaction mixture is thoroughly intermixed with external cooling.

In another embodiment of the invention, the individual components can be added separately into the reaction vessel and simultaneously intermixed there. In this embodiment, the mixing is carried in the turbulence of a pump which draws in the individual starting materials through 2 or 3 intake connections. Alternatively, the intermixing can also be carried out in a reaction vessel with built-in baffles, i.e. in a static mixer. Finally, the intermixing can also be carried out in an agitator vessel. In all such mixing vessels heat removal must however be ensured.

The reaction mixture is accordingly conveyed by the tube reactor into a heat-exchanger where reaction enthalpy is dissipated. According to a preferred embodiment of the invention, a plate heat-exchanger is used here. However, other types of heat-exchangers can also be used, e.g. the tube bundle heat-exchanger.

During the operation of the process, it has proven useful to monitor the temperature of the reaction mixture at several sections of the reaction apparatus so as to ensure by controlling the rate of flow of the whole mixture that the zone where the maximum reaction conversion occurs is in the portion of the apparatus where removal of heat can most effectively be carried out.

The reaction mixture is then fed from the heat-exchanger into a subsequent reaction zone. The subsequent reaction is only moderately exothermic. A stretch of the tube in the tube reactor can be utilized as the post-reaction zone. It is however also possible to carry out the subsequent reaction in an agitator vessel or a cascade of agitator vessels or even in a final mixing vessel.

It has proven useful in the reaction process to adjust the water content of the system as a whole to 45 to 60% by weight, preferably to 48 to 52% by weight. Both space-time consumption and the control of the reaction under industrial conditions are improved with this quantity of water.

A number of nitroparaffins can be used in the process of the invention. Nitroparaffins with 1 to 8 C-atoms are preferably used, particularly the lower molecular weight nitroparaffins, for example, nitromethane or its higher homologues with up to 4 C-atoms.

The fundamental reaction of the process of the invention is base-catalyzed. It has been found that the potassium salts of, e.g. 2-nitropropanediol dissolve so well in the reaction mixture under reaction conditions that there is no occurrence of the crystallizing-out effects noted with the corresponding sodium salts, which would complicate the passage of heat and therefore temperature control.

Short-chain aldehydes are preferably used as the aldehydes in the process according to the invention, particularly those with up to 3 C-atoms. Particularly preferred aldehydes are formaldehyde, acetaldehyde, and chloral, which can be used alone or in a mixture of two or even all three. The mixtures can be used with any proportions of the components thereof.

The process can be structured differently if nitromethane is used as the nitroparaffin and formaldehyde is used as the aldehyde. In this case when catalytic quantities of potassium hydroxide and an adequate quantity of formaldehyde are added, 2-(hydroxymethyl)-2-nitro-1,3-propanediol is obtained as the reaction product. This compound can be used as a microbicide or can be reduced to the corresponding amine which has many uses, e.g. as a buffer or in the lacquer industry.

When formaldehyde and nitromethane are used in the presence of stoichiometric quantities of potassium hydroxide, the potassium salt of 2-nitro-1,3-propanediol is produced. This compound can be processed further after neutralization to form known microbicides, e.g. 2-bromo-2-nitro-1,3- propanediol, or reduced to form the amine.

A strict control of temperature is required for the process of the invention. The process is carried out at a temperature between $-5°$ and $+20°$ C., and preferably at a temperature between 0° to 15° C.

The alkaline solutions obtained according to the invention are neutralized, provided they are not used as such for subsequent stages of the reaction, so as to avoid a reverse reaction. The nitroalcohols thus obtained, which are stable in neutral to acidic conditions, can then if desired be isolated, using known techniques.

According to a preferred embodiment of the process a mixture of aqueous aldehyde solution and the potassium hydroxide is prepared in a reaction vessel and circulated by a pump through a heat-exchanger, e.g. a plate heat-exchanger, into the initial reaction vessel. The nitroparaffin solution is added before the pump at a rate determined so that a maximum reaction temperature of 20° C., and preferably a maximum reaction temperature of 15° C. is not exceeded in the reaction mixture.

The invention will be illustrated but not limited by the following examples.

EXAMPLES

Example

Production of 2-nitro-propanediol-1,3-potassium salt

The process was carried out in a pilot plant, consisting of a 0.8 m$^3$ agitator container, a centrifugal pump with a throughput rate of 25 m$^3$.h$^{-1}$; H=40m, and a 12m$^2$ plate heat-exchanger.

229.2 kg of 37% by weight aqueous formaldehyde solution was placed in the agitator container and cooled to a temperature of 0° to 10° C. by pump circulation through the heat-exchanger and back into the agitator container. 201.4 kg of a 45% by weight aqueous potash lye was then added over 30 minutes; mixing took place in the turbulence of the centrifugal pump. The temperature of the mixture was held between 0° and 10° C.

82.1 kg of nitromethane was added to this mixture over 2 hours. The rate of addition was adjusted so that the temperature of the reaction mixture did not exceed 15° C. at any time. The temperature was regulated in part by the rate of addition of the nitromethane. The post reaction time was 15 minutes, and during this time the reaction mixture was pumped around the circuit. At the end of the reaction time the residual content of nitromethane had fallen to under 1% by weight. The potassium salt of the 2-nitro-1,3-propanediol which was formed remained in solution at temperatures down to $-15°$ C. 2-Nitro-1,3-propanediol was produced by neutralizing the salt solution.

Comparison Example

Example 1 was repeated, but instead of the potash lye the equivalent quantity of soda lye was used. As the reaction product, a suspension of the sodium salt was obtained in the reaction medium. Deposits were formed in some sections of the heat-exchanger which therefore had to be cleaned after every charge.

We claim:

1. In a process for the reaction of a nitroparaffin with an aqueous aldehyde by aldol condensation in the presence of a base, the improvement wherein
   (a) the reaction is carried out in the absence of organic solvents,
   (b) the reaction is carried out at a temperature in the range of from $-5°$ to $+20°$ C.,
   (c) the base is potassium hydroxide, and
   (d) from about 45 to about 60% by weight of the reaction mixture is water.

2. The process of claim 1 wherein the reaction is carried out with continuous mixing of the reaction mixture.

3. The process of claim 1 wherein the temperature is between about 0° and about $+15°$ C.

4. The process of claim 1, wherein the aqueous aldehyde is aqueous formaldehyde.

5. The process of claim 1 wherein the aqueous aldehyde and the potassium hydroxide are mixed together and cooled to a temperature in the range of from about 0° to about to about $+10°$ C., followed by the addition of the nitroparaffin thereto at a rate such that the reaction temperature is not exceeded.

6. The process of claim 1 wherein from about 48 to about 52% by weight of water is present in the reaction mixture.

7. The process of claim 1 wherein the nitroparaffin contains from 1 to 8 carbon atoms in the paraffin moiety thereof.

8. The process of claim 1 wherein the nitroparaffin is nitromethane.

9. The process of claim 4 wherein the nitroparaffin is nitromethane.

10. The process of claim 9 wherein catalytic quantities of potassium hydroxide are employed and the product is 2-hydroxymethyl-2-nitro-1,3-propanediol.

11. The process of claim 9 wherein molar quantities of potassium hydroxide are employed and the product is the potassium salt of 2-nitro-1,3-propanediol.

12. The process of claim 1 wherein the aqueous aldehyde is acetaldehyde or chloral.

13. The process of claim 1 wherein the nitroparaffin contains from 1 to 4 carbon atoms in the paraffin moiety thereof.

14. The process of claim 1 wherein the nitroparaffin, the potassium hydroxide, and the aqueous aldehyde are precooled to a temperature in the range of from $-5°$ to $+20°$ C.

15. The process of claim 7 wherein the aldehyde contains up to 3 carbon atoms.

16. In a process for the reaction of a nitroparaffin with an aqueous aldehyde by aldol condensation in the presence of a base, the improvement wherein
   (a) the reaction is carried out in the absence of organic solvents,
   (b) the reaction is carried out at a temperature in the range of from about 0° C. to about 15° C.,
   (c) the base is potassium hydroxide, (d) from about 45 to about 60% by weight of the reaction mixture is water, and
(e) the nitroparaffin, the potassium hydroxide, and the aqueous aldehyde are precooled to a temperature in the range of from about 0° C. to about 15° C.

17. The process of claim 16 wherein the nitroparaffin contains from 1 to 8 carbon atoms and the aldehyde contains up to 3 carbon atoms.

18. The process of claim 17 wherein from about 48 to about 52% by weight of water is present in the reaction mixture.

* * * * *